United States Patent
Beguin

(10) Patent No.: US 11,607,552 B2
(45) Date of Patent: Mar. 21, 2023

(54) METHOD AND ACTIVE IMPLANTABLE MEDICAL DEVICE FOR DETERMINING THE USABLE CAPACITY OF A BATTERY FOR SUCH A DEVICE

(71) Applicant: SORIN CRM SAS, Clamart (FR)

(72) Inventor: Emmanuel Beguin, Montigny-le-Bretonneux (FR)

(73) Assignee: Sorin CRM SAS, Clamart (FR)

( * ) Notice: Subject to any disclaimer, the term of this patent is extended or adjusted under 35 U.S.C. 154(b) by 183 days.

(21) Appl. No.: 17/108,907

(22) Filed: Dec. 1, 2020

(65) Prior Publication Data

US 2021/0162225 A1    Jun. 3, 2021

(30) Foreign Application Priority Data

Dec. 2, 2019 (FR) .................................. 1913604

(51) Int. Cl.
| | | |
|---|---|---|
| *A61N 1/372* | (2006.01) | |
| *G01R 31/388* | (2019.01) | |
| *A61N 1/37* | (2006.01) | |
| *A61N 1/378* | (2006.01) | |
| *H04W 72/0453* | (2023.01) | |

(52) U.S. Cl.
CPC ............ *A61N 1/37258* (2013.01); *A61N 1/37* (2013.01); *A61N 1/378* (2013.01); *A61N 1/3708* (2013.01); *A61N 1/37217* (2013.01); *G01R 31/388* (2019.01); *H04W 72/0453* (2013.01)

(58) Field of Classification Search
CPC .................................................... A61N 1/3708
See application file for complete search history.

(56) References Cited

U.S. PATENT DOCUMENTS

| | | |
|---|---|---|
| 4,715,381 A | 12/1987 | Moberg |
| 6,671,552 B2 | 12/2003 | Merritt et al. |
| | (Continued) | |

FOREIGN PATENT DOCUMENTS

| | | |
|---|---|---|
| JP | H09-117521 A | 5/1997 |
| JP | 2007-179968 A | 7/2007 |
| | (Continued) | |

OTHER PUBLICATIONS

French Search Report on French Application No. 1913604 dated Jul. 23, 2020.

(Continued)

*Primary Examiner* — George R Evanisko
(74) *Attorney, Agent, or Firm* — Foley & Lardner LLP

(57) ABSTRACT

A method for determining usable capacity of a battery of an active implantable medical device comprising a radiofrequency (RF) communication unit for transmitting data by RF over a communication period, wherein the usable capacity of the battery enables the active implantable medical device to transmit data by RF via the RF communication unit. The method includes measuring a value for the voltage of the battery which is representative of an instantaneous voltage drop of the battery as a result of a current draw on the battery, comparing the voltage of the battery with a predetermined threshold voltage VBS, and transmitting an alert message to a second device when the measured voltage of the battery crosses the predetermined threshold voltage.

19 Claims, 3 Drawing Sheets

(56) References Cited

U.S. PATENT DOCUMENTS

| | | | |
|---|---|---|---|
| 8,214,164 B2* | 7/2012 | Gandhi | A61N 1/3708 |
| | | | 320/132 |
| 2010/0010559 A1 | 1/2010 | Zhang et al. | |
| 2012/0109248 A1 | 5/2012 | Danielsson et al. | |
| 2014/0277286 A1* | 9/2014 | Cinbis | A61N 1/37276 |
| | | | 607/60 |
| 2015/0105842 A1 | 4/2015 | Lamont et al. | |

FOREIGN PATENT DOCUMENTS

| | | |
|---|---|---|
| JP | 2007-300154 A | 11/2007 |
| JP | 2013-542836 A | 11/2013 |
| JP | 2019-158694 A | 9/2019 |

OTHER PUBLICATIONS

Office Action issued in Japanese Application No. 2020-198055 dated Nov. 16, 2021.
Office Action issued in EP Application No. 20211294.2 dated Dec. 18, 2020.

* cited by examiner

METHOD AND ACTIVE IMPLANTABLE MEDICAL DEVICE FOR DETERMINING THE USABLE CAPACITY OF A BATTERY FOR SUCH A DEVICE

CROSS-REFERENCE TO RELATED PATENT APPLICATIONS

This application claims the benefit of and priority to French Patent Application No. 1913604, filed Dec. 2, 2019, which is incorporated by reference herein in its entirety.

BACKGROUND

The present invention relates to a method as well as to an active implantable medical device, in particular a cardiac stimulator or a neurostimulator, for determining the usable capacity of a battery of an active implantable medical device equipped with a radiofrequency (RF) link, in particular for communicating with another device, in particular another external, non-implantable device.

Active implantable devices may comprise a radiofrequency (RF) communication unit for enabling communication with another device, in particular an external device, for example a programmer used by a practitioner, a home monitor, a smartphone or any other device. Here, the term "communication" should be understood to mean any communication between the implantable device and another device, independently of whether there has or has not been a response from the other device.

For patients wearing an active implantable medical device with a RF communication feature, it is vital for the usable capacity of the battery of a device of this type to be able to be determined. Apart from the case of an implantable defibrillator, the battery of an implantable medical device is exposed to currents which are much higher during the course of a RF communication than when delivering the therapy. It is thus necessary to define an indicator which will trigger an alert informing medical personnel that the RF link can no longer be used. In fact, it is necessary for the practitioner to be informed of collapse of the RF communication feature so that the practitioner can then replace the device in order to continue monitoring the patient remotely.

It has been observed that the data for the battery provided by its manufacturer does not correspond to actual conditions of RF use. For this reason, as they stand, the data cannot be used for determining whether the capacity of the battery is sufficient for the RF. In fact, traditionally, the information provided concerns the open circuit voltage (or low load voltage or resting voltage) and the voltage when the battery is subjected to a large current, for example 5 mA to 30 mA, which is stable over a predefined period. These data may be used alone or jointly, but they cannot be applied to a dynamic current profile during RF communication which is characterized by large fluctuations of current linked to the communications protocol. Abiding by these data then leads to building in considerable margins which severely affect the usable capacity, or in fact leads to overestimating the usable capacity, running the risk of compromising the active implantable medical device when using the RF beyond a certain level of depletion.

Another known method consists of continuously measuring the voltage or impedance of the battery during a communication by RF in a manner such as to check whether it has reached a predetermined threshold. The load on the battery essentially occurs during remote monitoring or in the presence of a practitioner. For this reason, it is not sufficient to wait for the patient's next check-up by RF communication to know whether the state of the battery can still allow the RF link to be used. In fact, several months or even a year could go by between two check-ups. This could lead to the fact that the performance of the active implantable medical device could become degraded when the check-up has taken place, and so the battery is no longer capable of supporting that load, or indeed the RF link could be interrupted as soon as the threshold is reached.

When the limit of use of the RF link coincides with the recommended replacement time (RRT), it is necessary to precisely define the residual lifetime each time the active implantable medical device is interrogated. This residual lifetime indicator relies on an evaluation of the level of depletion of the battery. It is thus necessary to have an indicator which is reliable and available and updated very regularly, for example daily or weekly, while guaranteeing to the physician and the patient an optimized lifetime for use of the RF.

SUMMARY

The aim of the invention is to define a method which optimizes the determination of the usable capacity of the battery of an active implantable medical device which can be used to communicate with a programmer, a home monitor or any other device, in particular an external device, via a RF link.

The aim of the present invention is achieved by means of a method for determining the usable capacity of a battery of an active implantable medical device, in particular a cardiac stimulator, comprising a radiofrequency (RF) communication unit for transmitting data by RF over a communication period, and wherein the usable capacity of the battery of the active implantable medical device enables to transmit data by RF via the RF communication unit, the method comprising: a) a step for measuring a value for the voltage $VBi$ of the battery which is representative of an instantaneous voltage drop $dVBi$ of the battery of said device as a result of a current load on the battery, b) a step for comparing said voltage $VBi$ of the battery with a predetermined threshold voltage $VBS$, and c) a step for transmitting an alert message to another device when said measured voltage $VBi$ of the battery crosses the predetermined threshold voltage $VBS$.

The invention exploits the fact that the instantaneous drop in voltage when loading begins provides sufficient information to determine the capacity of the battery. This method can therefore be used to increase the lifetime of use of the battery of an active implantable medical device, in particular by dispensing with the considerable margins derived from the manufacturer's data which severely reduce the usable capacity. The observed instantaneous drop is in particular linked to the resistive portion of the battery.

The present invention, relating to a method for determining the usable capacity of a battery of an active implantable medical device, may be further improved by means of the following embodiments.

In accordance with one embodiment, the load may correspond to a current draw with a period of less than 20 ms, in particular less than 10 ms.

Thus, by applying a pulse with a duration which is shorter than the duration of a communication necessary for the transmission of data, it is possible to determine the usable capacity of the battery. For this reason, it is not necessary to have to use a complete transmission of data by RF in order to determine the usable capacity, i.e. to use a RF communication during remote check-ups or check-ups in the presence of a practitioner which, moreover, only take place once a year.

In accordance with one embodiment, step a) may comprise the measurement of at least one high peak voltage and the next low peak voltage of the voltage of the battery which oscillates between peak-peak values during a RF communication.

Thus, any type of RF communication of an implantable device, for example during "advertising" in accordance with the Bluetooth protocol or during a regular exchange between the device and any external apparatus, may be used in order to determine the state of the battery. The determination of the high and low values may be carried out at any time because the instantaneous drop between a high value and the next low value is primarily linked to the resistive portion of the battery which is substantially constant for a given state of depletion of the battery.

In accordance with one embodiment, step a) may furthermore comprise the measurement of the open circuit voltage of the battery before any loading.

Thus, even if the high and low peak voltages are measured during transmission, the measurement of the open circuit voltage may be used to normalize the measurement in order to be able to carry out the comparison with the predetermined threshold voltage VBS.

In accordance with one embodiment, the current draw may be shorter than the predetermined duration of the transmission of data by a factor of at least 100, in particular by a factor of at least 1000.

Thus, the battery is only slightly loaded in order to determine its usable capacity.

In accordance with one embodiment, the current draw may be produced with a peak current, corresponding to the maximum current present during a transmission of RF data.

Thus, the situation obtained is comparable to the transmission of data, which makes the method for determining whether the battery can still transmit data via RF even more reliable.

In accordance with one embodiment, the step for measuring the voltage VBi of the battery of said active implantable medical device may be carried out periodically, in particular daily.

Thus, the voltage VBi of the battery can be measured more regularly and the prediction of the lifetime can be evaluated and will be available for each interrogation, whether carried out remotely or in a hospital environment. In addition, because the current draw is of short duration, the impact on the lifetime of the battery is negligible. In fact, this is clearly not a question of periodically measuring the voltage of the battery which is subjected to a current draw of a duration equal to a transmission of data by RF. Thus, the lifetime of the device is not compromised in any substantial manner.

In accordance with one embodiment, the predetermined threshold voltage VBS may represent a threshold voltage which still allows at least one transmission of data by RF from said active implantable medical device to another device, in particular to another, non-implantable external device.

Thus, at least one alert message can still be transmitted to another device, in particular an external non-implantable device. It is then possible to warn medical personnel of this state of depletion of the battery.

In accordance with one embodiment, the predetermined threshold voltage VBS may be higher than a limiting voltage VBref which is representative of the operating limit of the RF communication circuit of said active implantable medical device.

Thus, the method provides a safety margin, ensuring at least the transmission of an alert message before the RF link can no longer be used.

In accordance with one embodiment, the current draw may be produced using the RF unit of said active implantable medical device.

Thus, the invention may be implemented with no supplemental source dedicated to the current necessary for the current drain.

In accordance with one embodiment, the generation of the current draw may comprise the generation of a carrier wave accompanied or not accompanied by activation of at least a portion of the functions necessary for the transmission of RF data.

For this reason, the current may be supplied via the RF unit by activating elements generating the peak current required during the transmission of RF data. Thus, the method can be used to generate a current comparable to that present during a transmission of RF data.

In accordance with one embodiment, the generation of the current draw comprises using a connection scan channel in order to initiate an RF communication of said active implantable medical device with another device, in particular using a primary advertising channel of the Bluetooth protocol.

For this reason, the current drain may be one of those already present in the connection scan protocol provided that the current is representative of the peak current during a RF communication. This also ensures that there is no interruption to communications present in the environment of the wearer of the active implantable medical device.

In accordance with a variation, the method may comprise a step for determining the residual capacity and/or the residual lifetime of the battery as a function of the measured voltage VBi.

This may be carried out by comparing the voltage VBi with tables stored in the memory of the active implantable medical device. In order to determine the residual lifetime, the usage of the battery in the past may be taken into consideration.

In accordance with one embodiment, the method may comprise the transmission of a message as a function of the residual capacity and/or the residual lifetime of the battery.

Thus, a message is transmitted, which means that a user or the processing personnel can know for how much longer transmission of data by RF will be possible.

In accordance with one embodiment, the method may comprise a step for transmission of the value VBi to another device upon the request of the other device and/or the user.

Thus, the residual capacity and/or residual lifetime may also be established outside the active implantable medical device. This reduces the need for memory and computing power in the active implantable medical device, thereby enabling the energy consumption and volume of the device to be reduced.

In accordance with one embodiment, the method may comprise a step for authorisation or not of automatic monitoring as a function of VBi.

Depending on the state of health of the user, the practitioner can program the implantable medical device in a manner such as to authorise the transmission of data by RF or otherwise. For a patient for whom transmission is not necessary, this feature is then not used, which means that the lifetime of the battery can be prolonged. However, following a degradation of the state of health of the user, the practitioner may decide that the automatic transmission of data by RF should be used. If at this time the value of VBi is already below the threshold VBS, the use of the RF feature will be blocked in order to prevent malfunction of the device.

In accordance with one embodiment, the transmission of RF data from the active medical device may be suspended following crossing of the predetermined threshold voltage VBS.

Thus, the active medical device may still be used without this feature until another parameter is reached, such as the recommended replacement time.

The aim of the present invention is also achieved by means of an active implantable medical device equipped with a RF link comprising a battery, a RF unit and a controller. The controller is configured in order to carry out the method as described above.

Thus, it is possible to determine the usable capacity of the battery by the application of a pulse with a duration which is shorter than the duration of a communication necessary for the transmission of RF data. For this reason, it is not necessary to have to invoke a complete transmission of RF data in order to determine the usable capacity, i.e. to use a RF communication during remote monitoring or in monitoring in the presence of a practitioner, which can in addition only take place once a year. In other words, by means of the active implantable medical device of the invention, there is no need to establish a RF communication in order to determine whether data transmission is still possible. In addition, because the duration of the current draw is shorter than that of a transmission of data by RF, the impact on the lifetime of the battery is negligible. It is therefore possible to increase the battery life of the active implantable medical device, in particular by doing away with the considerable margins which are derived from the manufacturer's data, which severely affects the usable capacity.

BRIEF DESCRIPTION OF THE DRAWINGS

The invention and its advantages will now be explained in more detail below by means of preferred embodiments, in particular made with reference to the accompanying figures, in which.

DETAILED DESCRIPTION

Figure 1:
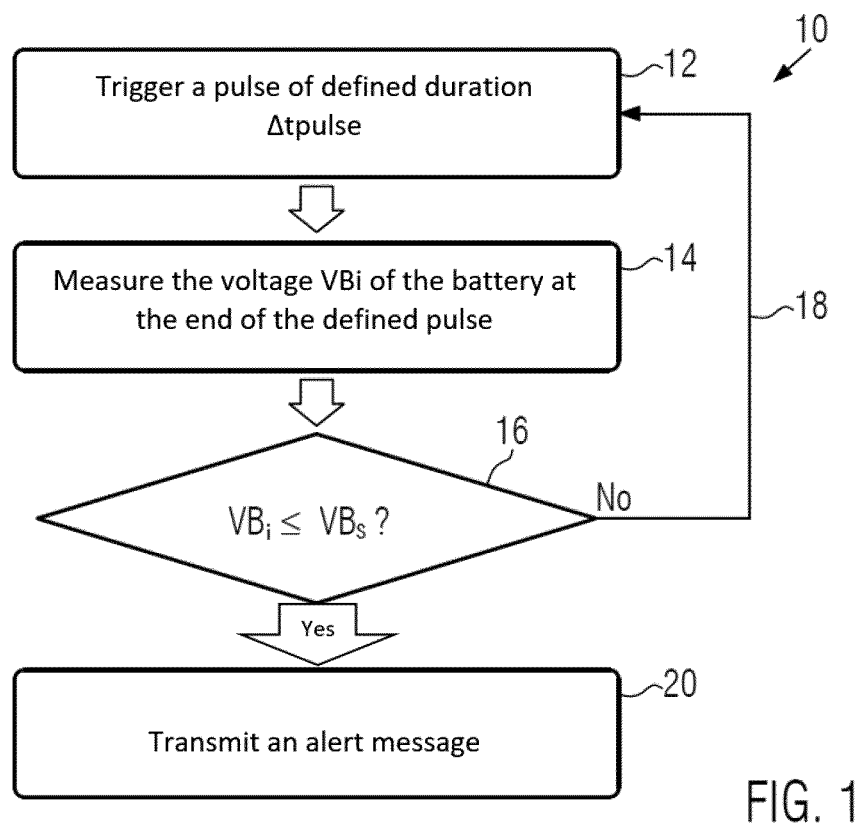
FIG. 1 represents an organigram of a method in accordance with the present invention for determining the usable capacity of a battery of an active implantable medical device.

In order to ensure that the battery of an active implantable medical device with a radiofrequency communication feature RF is still capable of providing the power necessary for the transmission of RF data, the invention proposes a method which can be used to regularly check the state of the battery, for example daily, without loading the battery itself too much. The conditions for RF transmission are typically predetermined, and the transmission speed, the size of the memory pool to be transmitted and the duration of the communication are known. There are various types of RF communication such as, for example, periodic wakeup with a brief communication from a duration of a few milliseconds to several tens of milliseconds in order to check whether or not a communication is necessary (for example by using the "advertising" mode of the Bluetooth standard). A communication by RF may also act to send a message in order to indicate whether or not to communicate with another device. It may be a communication with transmission of data with a duration of less than one second. Finally, it may be a communication with transmission of data which may last several tens of seconds.

The method in accordance with one embodiment of the present invention for determining the usable capacity of a battery of an active implantable medical device will be described with the aid of the organigram of FIG. 1.

During a first step 12 of the method 10 in accordance with the present invention, a defined current draw with a duration $\Delta$tpulse and an intensity which is representative of a peak current required by the transmission of data by RF from an active implantable medical device is triggered. The current draw has a duration $\Delta$tpulse of less than 20 ms, in particular less than 10 ms, so that it is sufficiently short to substantially correspond to an instantaneous drop in the battery voltage.

Hence, the duration of the current draw is shorter than the duration of the transmission of RF data. For a typical transmission of RF data of a stimulator, this duration is shorter by a factor of at least 100, more particularly by a factor of at least 1000.

During a second step 14 of the method 10 in accordance with the invention, the VBi (also indicated as $VB_i$ on the drawings) of the battery is measured at the end of the current draw triggered in step 12. This voltage is representative of the instantaneous drop in the battery following loading of the battery.

During a third step 16 of the method 10 in accordance with the present invention, the measured voltage VBi is compared with a predetermined threshold voltage of the battery, VBS (also indicated as $VB_s$ on the drawings).

If the voltage VBi measured at the end of the current draw is greater than the predetermined threshold voltage for the battery, VBS, this means that the battery of the active implantable medical device still has usable capacity for ensuring the transmission of data by RF. As soon as this threshold is crossed, complete transmission of data by RF can no longer be guaranteed. As indicated by the arrow 18, the method 10 then returns to step 12. Step 12 may be repeated at intervals which are close together, for example once a day.

It should be noted that the value of the predetermined threshold voltage for the battery, VBS, is fixed throughout the lifetime of the battery. Thus, it is not necessary to determine afresh the value of the predetermined threshold voltage for the battery, VBS.

In the case in which the voltage VBi measured at the end of the current draw is less than or equal to the predetermined threshold voltage for the battery, VBS, an alert message is transmitted during a step 20 in order to warn the medical personnel or user that the battery has reached the predetermined threshold voltage of the battery, VBS, which might or might not necessitate an exchange of the implantable medical device, depending on whether the threshold VBS is or is not the same as the recommended replacement time.

In accordance with a variation, the voltage VBi may act as a reference in order to determine the residual capacity of the battery for use of the RF, and thus act as a basis for determining the residual lifetime for use of the RF before reaching the voltage VBS.

Given that the voltage VBi is measured regularly, for example daily, this residual lifetime is available and up to date each time the active implantable medical device is interrogated, whether this is carried out remotely or in fact in the presence of a practitioner. Thus, the value VBi may be transmitted to another device which may determine the residual capacity and/or the residual lifetime from tables or from an algorithm. In accordance with a variation, the residual capacity or the residual lifetime may also be determined in the active medical device.

It should be noted that if stopping the use of the RF coincides with the recommended replacement time, the voltage VBi may act as a reference for the residual lifetime indicator of the active implantable medical device.

If stopping the use of the RF does not coincide with the recommended replacement time, crossing the threshold will cause the RF feature to stop. However, the active medical device can still be used until the recommended replacement time. If the state of health of the user allows it, the device can then still be used, thereby delaying the time when the device has to be changed.

In accordance with another way of using the voltage VBi, reaching the voltage VBS may also act to not authorise programming of remote monitoring for the future for a device which was not so before.

Because it is not necessary to periodically measure the voltage of the battery which is subjected to a current draw with a duration equal to a transmission of RF data, the determination of the usable capacity has a lesser impact on the lifetime of the battery. In fact, because the current draw is of short duration compared with the duration of a transmission of RF data, the impact of a current draw of this type on the lifetime of the battery is negligible. In addition, the method 10 can be used to carry out a periodic measurement, for example daily, and can be used for non-urgent replacement of the active implantable medical device when required.

The present invention also concerns an active implantable medical device equipped with a RF link comprising a battery, a RF unit and a controller. The controller is configured to determine the usable capacity in accordance with the method 10 as described with reference to FIG. 1.

Figure 2:
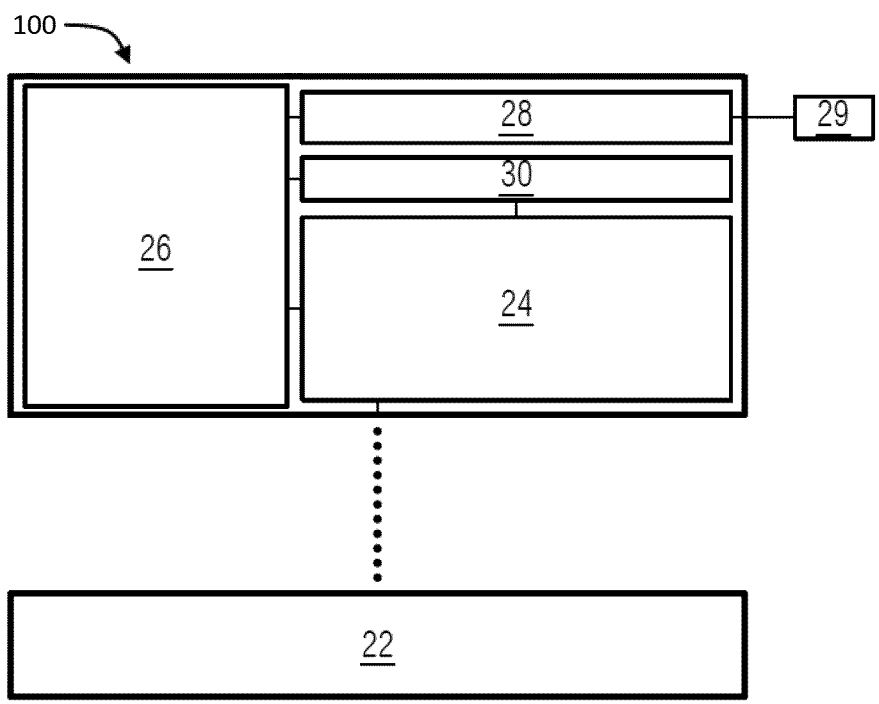
FIG. 2 represents an active implantable medical device in accordance with the present invention.

FIG. 2 illustrates an active implantable medical device 100 of this type, configured in accordance with the invention. The active implantable medical device 100 is configured in order to be able to produce a wireless link of the radiofrequency RF type with another device, in particular with another external device 22. The implantable medical device 100 may be a cardiac stimulator or a neurostimulator. The other device, in particular the external device 22, may be a programmer used by a clinical practitioner, a home monitor or any other device.

The active implantable medical device 100 comprises a radiofrequency unit (RF) 24 enabling communication with the other device, in particular with the other external device 22. It comprises a battery 26 for allowing RF communication. The battery 26 also supplies the energy necessary for delivering a therapy produced via a controller 28 which manages one or more electrodes 29. In addition, the active implantable medical device 100 comprises a controller 30 which is configured in order to determine the state of the battery 26 in accordance with the method 10 described below. Thus, the state of the battery 26 is determined by means of a short current draw with a duration Δtpulse which is less than 20 ms in duration, in particular less than 10 ms, so that it is shorter than the duration of a usual transmission of RF data from the device 100 and used to transmit data to the other device, in particular to the other external device 22.

In accordance with an advantageous variation, the current draw may be implemented by using the RF unit 24 of said active implantable medical device 100. In this case, the current is supplied via the RF unit 24 by activating elements generating the peak current required during a transmission of RF data. The interest is in generating an identical current and of not having to call upon a supplemental source of current. The peak current is obtained by generating the carrier wave and activating the other functions, necessitating a significant current during a transmission of RF data.

In accordance with another variation, the controller 30 is configured to use the communication protocol, in particular the connection scan protocol, to generate the current draw. For this reason, the method 10 may be carried out with features which are already available in the active implantable medical device 100.

Figure 3:
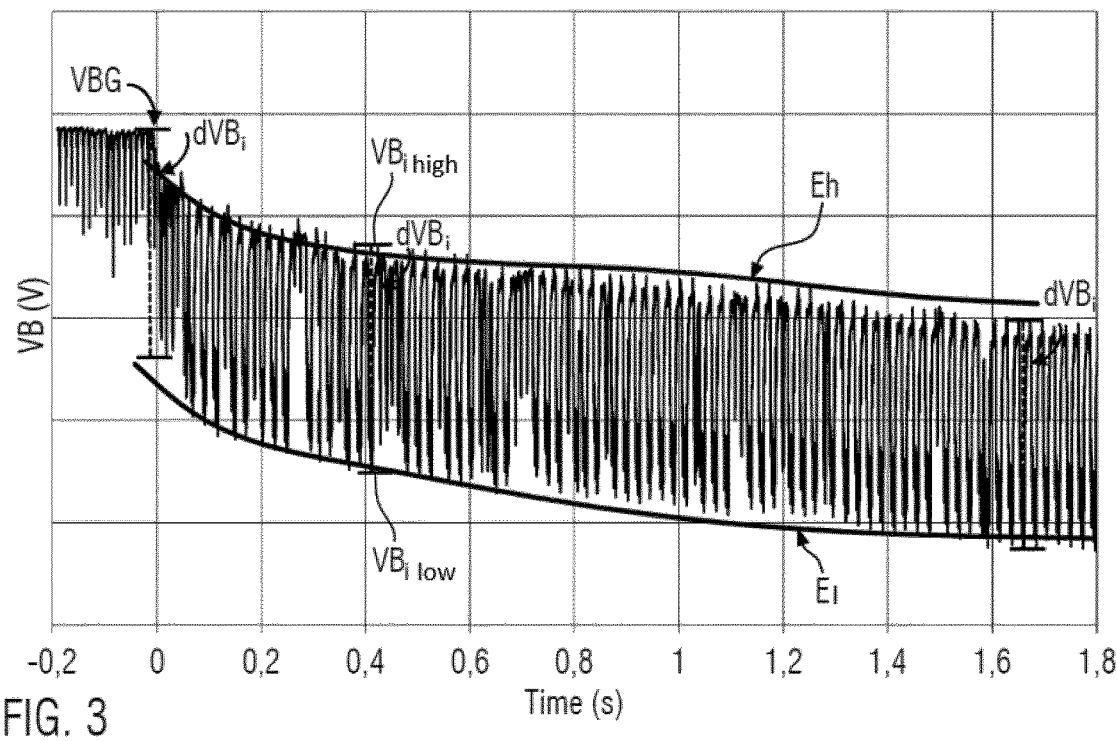
FIG. 3 illustrates a graph representing the voltage in the battery subjected to current draws during a transmission of RF data.

FIG. 3 illustrates a graph representing the voltage of a battery which is subjected to current draws as a function of time and representative of the start of a transmission of RF data.

The behaviour of a battery when it is subjected to a regime of dynamic current draws of a transmission of RF data, for example by using the Bluetooth protocol or any other RF communication protocol which is suitable, results in an instantaneous voltage drop on each current draw, which is pronounced to a greater or lesser extent as a function of the filtering capacity generally connected to the battery. This instantaneous drop is primarily linked to the resistive portion of the battery which, for a given state of depletion of the battery, may be considered to be a constant.

As can be seen in FIG. 3, the voltage of the battery VB oscillates between a high peak voltage VBi high and a following low peak voltage VBi low during a transmission of RF data.

A gradual drop with the RF communication or the transmission of RF data will also be observed. The profile of the voltage of the battery is thus linked to a higher current, also termed the peak current which creates these instantaneous voltage drops, and to a mean current supplied to produce the transmission of RF data, which is the basis of the gradual voltage drop.

The instantaneous relative voltage drop denoted dVBi in FIG. 3 (also indicated as $dVB_i$ on the drawings) occurs at each current draw throughout the transmission of RF data. Thus, at the moment of loading the battery at time t=0, the instantaneous drop dVBi is the same as that a little later, for example at 0.4 s or at 1.65 s. The battery voltage reached at the end of a transmission of RF data thus depends on the instantaneous current responsible for the instantaneous drops and on the mean current responsible for its gradual drop. Two parameters can thus be defined: the first parameter, illustrated in FIG. 3, is the voltage of the battery at the end of a single current draw which is short, representative of the instantaneous voltage drop dVBi during a peak current, and the second parameter is the voltage at the end of a single current draw with a predefined duration which is equal to the transmission of RF data and current equal to the peak current, which will be explained in more detail with respect to FIGS. 4 and 5.

Here, for the first parameter, the term "short duration current draw" should be understood to mean a duration which is at least equal to the duration of the current draws which are responsible for the instantaneous drop in the battery voltage, i.e. of the order of 1 ms and at most a duration which does not exceed 20 ms. Beyond this, the drop in voltage becomes higher and less and less representative.

Typical values for a maximum peak current during a transmission of RF data for an active implantable medical device such as a cardiac stimulator are of the order of 5 mA to 30 mA; a mean current is of the order of 2 mA to 10 mA and the duration of a RF communication for a complete transfer of data stored in the memory of an implant is of the order of 10 s to 60 s.

Figure 4:
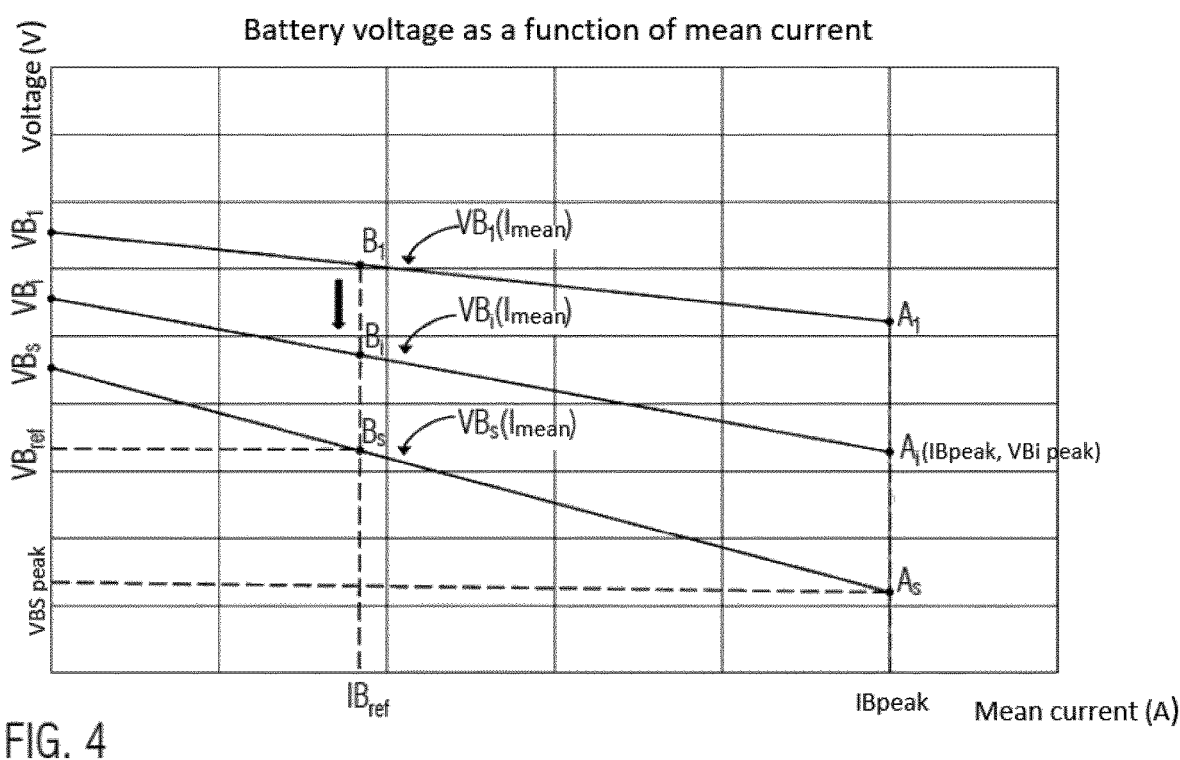
FIG. 4 illustrates a graph representing the voltage of a battery as a function of the mean current when it is subjected to current draws for a duration which is representative of a transmission of RF data.

FIG. 4 illustrates a graph representing the voltage of the battery at the end of a transmission of RF data for a defined duration up the ordinate as a function of the intensity of the mean current drawn from the battery during the transmission of RF data along the abscissa and as a function of the depletion of the battery. The relationship between the voltage at the end of the transmission of RF data and the mean current is linear to a first approximation.

In FIG. 4, the voltage VBi, with i=1 to n, corresponds to the voltage of the battery after the instantaneous voltage drop following loading of the battery.

For the short current draw, the current with respect to the duration of a transmission of RF data is negligible, and so the instantaneous drop can thus be placed at the origin of the abscissa. VBi then corresponds to the voltage observed at the end of the defined short current draw with duration Δtpulse.

In contrast, the higher the mean current, the closer it approaches the peak current. By linear approximation, the straight line is extended to a point corresponding to the peak current (IBpeak). Thus, this point corresponds to a current draw for the duration of the transmission of RF data wherein the current is constant and equal to the peak current.

The point Ai, i=1 to n, with coordinates (IBpeak; VBi peak) on the graph of FIG. 4 corresponds to the current draw with a duration equal to that of a transmission of RF data with the mean current of the transmission being equal to the peak current IBpeak, i.e. to the maximum instantaneous current that the battery supplies during the entirety of the predetermined duration for a transmission of RF data.

Depending on the parameterization of the RF communication of the device, the mean current is thus between the two limiting values I=0 and I=IBpeak. To a first approximation, the voltage of the battery will be on the straight line connecting the two extreme points Ai and (0, VBi).

Depending on the depletion of the battery, the plot VBi (Imean) is displaced gradually downwards, as indicated by the arrow and a second straight line defined by the points Ai and (0, VBi). It will be observed that the voltage drop VBipeak as a function of the depletion is greater as the voltage VBi drops. This necessarily implies that from a certain level of depletion, a limiting voltage of the battery will be reached for which the transmission of RF data operation will no longer be guaranteed. A prediction of good and reliable operation of the active implantable medical device and with an optimization of the usable capacity of the battery is thus the aim of the invention.

The invention is based on the fact that the manufacturer of the battery is capable of supplying the change in the battery voltage for a given peak current and the durations corresponding to the short current draw and to the determined duration corresponding to that of the transmission of data, and thus the values VBi and Ai. By means of these manufacturer's data, it is possible to obtain the straight lines VBi(Imean) illustrated in FIG. 4 as a function of the depletion of the battery. In addition, it becomes possible to define the level of depletion of the battery for which the straight line defined by AS (also indicated as $A_s$ on the drawings) and VBS passes through the point BS (also indicated as $B_s$ on the drawings) corresponding to the limiting voltage for which the operation of the transmission of RF data is guaranteed (VBref), and the mean current (IBref).

The mean current IBref for a transmission of RF type data from the stimulator may be determined experimentally. In addition, the design of the given implantable medical device also means that a limiting voltage VBref which is necessary for proper operation and in particular for ensuring the RF link can be defined. This voltage may also be determined experimentally. These values then determine the point BS, illustrated in FIG. 4.

Assuming a linear dependency between the voltage and mean current, extrapolation of the straight line VBS(Imean) passing through the points AS and BS towards the origin of the abscissa will provide the limiting voltage VBS which is not to be exceeded after application of a short current draw.

Thus, it now suffices to compare the voltage VBi representing the voltage of the battery measured at the end of a short current draw of short duration, Δtpulse, with the threshold of the limiting voltage VBS of the battery in order to determine whether the usable capacity of the battery is still sufficient. Since the load on the battery is very short in order to be able to determine VBi, the test can be carried out regularly and frequently, for example daily.

Given the energy required, periodically measuring VBipeak in order to take into account the point AS for each battery used in the active implantable medical device in order to be able to determine the threshold voltage VBS cannot be envisaged; it is more advantageous to establish a common threshold for a plurality of batteries for active implantable medical devices of the same type. Thus, it is not necessary to determine VBSpeak afresh for each device.

For safety reasons, the voltage VBSpeak selected in order to establish the straight line VBS(Imean) corresponds to the voltage VBpeak with the lower voltage for the same peak current IBpeak observed for a series of batteries of the same type. In other words, the voltage VBSpeak taken into account as the reference may correspond to the "worst case" battery in order to introduce a safety margin. This battery will have a straight line VBS(Imean) which passes through the point BS and which will have the largest decrease.

The threshold voltage of the battery, VBS, defined by the reference straight line VBS(Imean) acts as a reference point for the battery assembly. Because of the safety margin introduced by the reference straight line VBS(Imean), the threshold voltage for the battery, VBS, means that the limiting operational voltage, VBref, of the battery cannot be reached at the moment when the threshold voltage VBS is reached during measurement on the short current draw. In fact, depending on the level of depletion of the battery, the measured voltage of the battery VBi at the end of a short current draw will reduce from the value VB1 to the value VBS, which ensures that the battery voltage reached at the end of a transmission of RF data remains above VBref. Successive straight lines connecting the points Ai and the point (0; VBi) will be displaced in a manner such as to drop towards the abscissa and approach the reference straight line VBS(Imean) as a function of the depletion of the battery. At the moment the threshold voltage VBS is reached, it will be possible to carry out one more transmission of data by RF from the active implantable medical device to another device, in particular to another external non-implantable device. This may preferably be a transmission of RF data, which enables all useful information to be transmitted, and in particular enables the transmission of data present in the memory. In accordance with an alternative, it may also be an alert message in order to warn medical personnel of this stage of depletion of the battery.

For this reason, the safety margin introduced by the reference straight line VBS(Imean) ensures at least RF data or an alert message to be transmitted before the RF link can no longer be used. It should be noted that the voltage VBS acts as a reference for the predetermined threshold voltage for a plurality of active implantable medical devices. Thus, it is not necessary to redefine VBS for each device.

Figure 5:
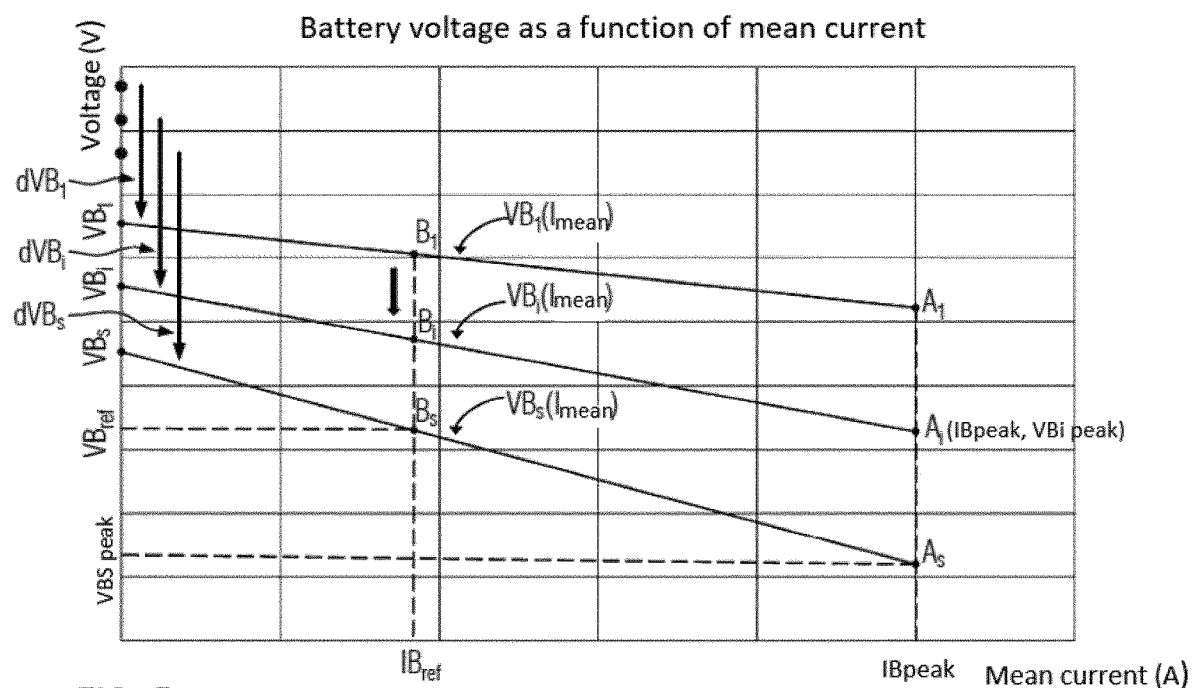
FIG. 5 illustrates a graph representing the voltage of a battery as a function of the mean current when it is subjected to current draws for a duration which is representative of a transmission of RF data and the determination of dVBi when the measurement is not made at the start of a transmission of RF data.

FIG. 5 illustrates a graph representing the voltage of a battery as a function of the mean current when it is subjected to current draws for a duration representative of a transmission of RF data and the determination of dVBi when the measurement is neither made at the start of a transmission of RF data nor by means of a current load specific to the measurement of VBi.

As already mentioned above, the instantaneous voltage drop, denoted dVBi in FIG. 3, is found at each current draw throughout the transmission of RF data. Thus, at the moment of loading the battery at the time t=0, the instantaneous drop dVBi is the same as a little later on, at 0.4 s or 1.65 s.

Thus, in accordance with an alternative, the method as described with respect to FIGS. 1 and 2 can also be carried out with any instantaneous drop during a transmission of RF data. By measuring a high peak voltage 'VBi high' and the next low peak voltage 'VBi low' of the battery voltage VB which oscillates between the high and low values during a transmission of RF data, for example at 0.4 s in FIG. 3, the value dVBi may also be determined. In contrast, the value VBGi, the open circuit voltage of the battery at the time of measurement, also has to be taken into account in order to obtain the value VBi. In fact, VBi=VBGi−(VBi high−VBi low).

As can be seen in FIG. 3, the open circuit voltage VBG also drops as a function of the state of depletion of the battery.

In order to reduce the margin of error, it is also possible to determine dVBi at several times during the transmission of RF data or to determine an envelope Eh which passes through the high values and another envelope El which passes through the low values and to determine the distance between the two.

What is claimed is:

1. A method for determining usable capacity of a battery of an active implantable medical device comprising a radiofrequency (RF) communication unit for transmitting data by RF over a communication period, wherein the usable capacity of the battery enables the active implantable medical device to transmit data by RF via the RF communication unit, the method comprising:
performing an electrical current draw on the battery over a period of time of less than 20 ms;
measuring a value for a voltage of the battery during an instantaneous voltage drop of the battery, the instantaneous voltage drop resulting from the electrical current draw on the battery;
comparing the voltage of the battery with a predetermined threshold voltage; and
transmitting an alert message to a second device when the measured value for the voltage of the battery crosses the predetermined threshold voltage.

2. The method of claim 1, further comprising determining a predetermined duration of a RF transmission, wherein the electrical current draw is shorter than the predetermined duration of the RF transmission by a factor of at least 100.

3. The method of claim 1, wherein the voltage of the battery oscillates between peak-peak values, and wherein measuring the value for the voltage further comprises measuring at least one of a high peak voltage and a subsequent low peak voltage of the battery.

4. The method of claim 3, wherein measuring the value for the voltage further comprises measuring an open circuit voltage of the battery before any loading.

5. The method of claim 1, further comprising determining a current present during a transmission of RF data, and wherein performing the electrical current draw includes producing a peak current corresponding to a maximum current present during the transmission of RF data.

6. The method of claim 1, further comprising implementing the method on a daily basis.

7. The method of claim 1, further comprising determining a threshold voltage that allows at least one RF transmission from the active implantable medical device to the second device, wherein the predetermined threshold voltage represents the threshold voltage.

8. The method claim 1, wherein the predetermined threshold voltage is higher than a limiting voltage, the limiting voltage corresponding to an operating limit of the RF communication unit of the active implantable medical device.

9. The method of claim 1, wherein the RF communication unit performs the electrical current draw.

10. The method of claim 9, wherein performing the electrical current draw comprises generating a carrier wave, accompanied or not accompanied by activating at least a portion one or more functions necessary for a transmission of RF data.

11. The method of claim 9, wherein performing the electrical current draw comprises using a connection scan channel to initiate an RF communication between the active implantable medical device and the second device.

12. The method of claim 1, further comprising determining at least one of a residual capacity or a residual lifetime of the battery based on the measured value for the voltage of the battery.

13. The method of claim 12, further comprising transmitting a message based on at least one of the residual capacity or the residual lifetime of the battery.

14. The method of claim 1, further comprising:
receiving a request from at least one of the second device or a user; and
transmitting a value of the voltage of the battery to the second device based on the request.

15. The method of claim 1, further comprising selectively authorizing automatic monitoring as a function of the voltage of the battery.

16. The method of claim 1, further comprising suspending transmission of RF data from the active implantable medical device in response to the voltage of the battery exceeding the predetermined threshold voltage.

17. The method of claim 1, wherein the active implantable medical device is a cardiac stimulator.

18. An active implantable medical device comprising a radiofrequency unit, a battery, and a controller, wherein the controller is configured to:

perform an electrical current draw on the battery over a period of time of less than 20 ms;

measure a value for a voltage of the battery during an instantaneous voltage drop of the battery, the instantaneous voltage drop resulting from the electrical current draw on the battery;

compare the voltage of the battery with a predetermined threshold voltage; and transmit an alert message using the radiofrequency unit to another device when the measured value for the voltage of the battery crosses the predetermined threshold voltage.

19. The active implantable medical device of claim 18, wherein the active implantable medical device is a cardiac stimulator.

* * * * *